(12) United States Patent
Mazor et al.

(10) Patent No.: US 7,453,985 B2
(45) Date of Patent: Nov. 18, 2008

(54) CONTROL OF X-RAY BEAM SPOT SIZE (75) Inventors: Isaac Mazor, Haifa (IL); David Berman, Kiryat Tivon (IL)

(73) Assignee: Jordan Valley Semiconductors Ltd., Migdal Ha'emek (IL)

( * ) Notice: Subject to any disclaimer, the term of this patent is extended or adjusted under 35 U.S.C. 154(b) by 0 days.

(21) Appl. No.: 11/822,231

(22) Filed: Jul. 3, 2007

(65) Prior Publication Data
US 2008/0043914 A1 Feb. 21, 2008

Related U.S. Application Data (63) Continuation-in-part of application No. 11/503,979, filed on Aug. 15, 2006, now Pat. No. 7,406,153.

(51) Int. Cl.
*G01N 23/201* (2006.01)
(52) U.S. Cl. .............................. 378/86; 378/89; 378/205
(58) Field of Classification Search ............. 378/70–90, 378/205, 207; 250/252.1
See application file for complete search history.

(56) References Cited

U.S. PATENT DOCUMENTS

| | | | |
|---|---|---|---|
| 4,725,963 A | 2/1988 | Taylor et al. |
| 4,989,226 A | 1/1991 | Woodbury et al. |
| 5,151,588 A | 9/1992 | Kiri et al. |
| 5,574,284 A | 11/1996 | Farr |
| 5,619,548 A | 4/1997 | Koppel |
| 5,740,226 A | 4/1998 | Komiya et al. |
| 5,923,720 A | 7/1999 | Barton et al. |
| 5,949,847 A | 9/1999 | Terada et al. |
| 6,041,098 A | 3/2000 | Touryanski et al. |
| 6,192,103 B1 | 2/2001 | Wormington et al. |
| 6,226,347 B1 | 5/2001 | Golenhofen |
| 6,226,349 B1 | 5/2001 | Schuster et al. |
| 6,381,303 B1 | 4/2002 | Vu et al. |
| 6,389,102 B2 | 5/2002 | Mazor et al. |
| 6,453,006 B1 | 9/2002 | Koppel et al. |
| 6,507,634 B1 | 1/2003 | Koppel et al. |
| 6,512,814 B2 | 1/2003 | Yokhin et al. |

(Continued)

FOREIGN PATENT DOCUMENTS

JP 09308339 12/1997

(Continued)

OTHER PUBLICATIONS

Jones, et al., "Small angle x-ray scattering for sub-100 nm pattern characterization", Applied Physics Letters 83:19 (2003), pp. 4059-4061.

(Continued)

*Primary Examiner*—Jurie Yun
(74) *Attorney, Agent, or Firm*—Smith, Gambrell & Russell, LLP (57) ABSTRACT

A method for analysis of a sample includes directing a beam of radiation to impinge on a target area on a surface of the sample along a beam axis at a plurality of different elevation angles. For each of the different angles, a respective offset of the beam in a direction transverse to the beam axis is determined. While sensing the radiation scattered from the sample at each of the different elevation angles in succession, a transverse correction is applied to at least one of the beam and the sample in order to compensate for the respective offset at each of the different elevation angles.

17 Claims, 8 Drawing Sheets

U.S. PATENT DOCUMENTS

| | | | |
|---|---|---|---|
| 6,556,652 | B1 | 4/2003 | Mazor et al. |
| 6,625,250 | B2 | 9/2003 | Houge |
| 6,639,968 | B2 | 10/2003 | Yokhin et al. |
| 6,643,354 | B2 | 11/2003 | Koppel et al. |
| 6,680,996 | B2 | 1/2004 | Yokhin et al. |
| 6,711,232 | B1 | 3/2004 | Janik |
| 6,744,950 | B2 | 6/2004 | Aleksoff |
| 6,750,952 | B2 | 6/2004 | Grodnensky et al. |
| 6,771,735 | B2 | 8/2004 | Janik et al. |
| 6,813,338 | B2 | 11/2004 | Takata et al. |
| 6,895,075 | B2 | 5/2005 | Yokhin et al. |
| 7,242,743 | B2 | 7/2007 | Fewster |
| 2001/0028699 | A1 | 10/2001 | Iwasaki |
| 2001/0043668 | A1 | 11/2001 | Hayashi et al. |
| 2002/0097837 | A1 | 7/2002 | Fanton et al. |
| 2002/0110218 | A1 | 8/2002 | Koppel et al. |
| 2003/0157559 | A1 | 8/2003 | Omote et al. |
| 2004/0052330 | A1 | 3/2004 | Koppel et al. |
| 2004/0156474 | A1 | 8/2004 | Yokhin et al. |
| 2004/0218717 | A1 | 11/2004 | Koppel et al. |
| 2006/0062351 | A1 | 3/2006 | Yokhin et al. |

OTHER PUBLICATIONS

Stommer, "X-ray scattering from silicon surfaces", in Semiconductor International (May 1, 1998).

Yoneda, "Anomalous surface reflection of X Rays", Physical Review 131, pp. 2010-2013, 1963.

Stommer, et al., "Characterization of semiconductor materials by X-ray scattering", Electrochemical Society Proceedings vol. 99-16, pp. 117-133, 1999.

Bowen, et al., "X-Ray metrology by diffraction and reflectivity", Characterization and Metrology for ULSI Technology, 2000 International Conference (American Institute of Physics, 2001).

Ulyanekov, "Introduction to high resolution X-Ray diffraction", Workshop on X-ray characterization of thin layers (Uckley, May 21-23, 2003).

Naudon, et al., "New apparatus for grazing X-ray reflectometry in the angle-resoived dispresive mode", J. Appl. Cryst. 1989, vol. 22, pp. 46-464.

F. Neissendorfer, et al., "The Energy-dispersive reflectometer/diffractometer at BESSY-I", Meas. Sci. Technol. 10(1999) 354-361.

A.R. Powell, et al., "X-ray diffraction and reflectivity characterization of SiGe superlattice structures", Semicond. Sci. Technol. 7(1992), 627-631.

CONTROL OF X-RAY BEAM SPOT SIZE

CROSS-REFERENCE TO RELATED APPLICATION

This application is a continuation-in-part of U.S. patent application Ser. No. 11/503,979, filed Aug. 15, 2006 now U.S. Pat. No. 7,406,153, whose disclosure is incorporated herein by reference.

FIELD OF THE INVENTION

The present invention relates generally to analytical instruments, and specifically to instruments and methods for material analysis using X-rays.

BACKGROUND OF THE INVENTION

X-ray reflectometry (XRR) is a well-known technique for measuring the thickness, density and surface quality of thin film layers deposited on a substrate. X-ray reflectometers typically operate by irradiating a sample with a beam of X-rays at grazing incidence, i.e., at a small angle relative to the surface of the sample, in the vicinity of the total external reflection angle of the sample material. An X-ray detector, which may comprise a detector array, senses the reflected X-rays. Measurement of X-ray intensity reflected from the sample as a function of angle gives a pattern of interference fringes, which is analyzed to determine the properties of the film layers responsible for creating the fringe pattern. Exemplary systems and methods for XRR are described in U.S. Pat. Nos. 5,619,548; 5,923,720; 6,512,814; 6,639,968, and 6,771,735, whose disclosures are incorporated herein by reference.

The spot size and angular extent of the X-ray beam that is incident on the sample surface affect the spatial and angular resolution of XRR measurement results. In order to control these factors, U.S. Pat. No. 6,639,968, for example, provides a dynamic knife edge and shutter interposed in the X-ray beam. For measurements at low incidence angles, the knife edge is lowered very near to the surface, intercepting the incident X-ray beam and thus shortening the lateral dimension of the spot on the surface. (In the context of the present patent application and in the claims, the dimension of the spot in the direction along the surface that is parallel to the projection of the beam axis on the surface is referred to in the conventional manner as the lateral dimension, while the dimension in the direction perpendicular to the beam axis is referred to as the transverse dimension.) For high-angle measurements, at which the dynamic shutter is used, the knife edge may be raised out of the way, to allow the full intensity of the X-ray beam to be used. As another example, U.S. Pat. No. 6,771,735 uses two "gates" for blocking certain parts of the X-ray beam.

U.S. Pat. No. 6,895,075, whose disclosure is incorporated herein by reference, describes a system that combines XRR with small-angle X-ray scattering measurement (SAXS). The system uses the dynamic knife edge and shutter of U.S. Pat. No. 6,639,968 for controlling the incident beam in the vertical direction (perpendicular to the surface of the sample), together with a slit for limiting the transverse dimension of the beam in the horizontal direction. The minimum slit width is said to be about 100 μm.

U.S. Patent Application Publication 2006/0062351, whose disclosure is incorporated herein by reference, describes another multifunction X-ray analysis system, which combines XRR with SAXS and X-ray diffraction (XRD) measurement. In one embodiment, shown in FIG. 5 of this publication, a knife edge is made of a cylindrical, X-ray absorbing material, such as a metal wire. This arrangement is said to permit the lower edge of the knife to be placed very close to the surface of the sample, on the order of 3 μm above the surface, without risk of damaging the sample. The wire can be aligned with the surface accurately and thus provides a small gap above the surface whose effective height is uniform over the entire angular range of interest, typically 0-4°. Based on this example, it will be understood that in the context of the present patent application and in the claims, the term "knife edge" refers to any type of straight edge (not necessarily very sharp) that is positioned near the surface of a sample in order to create this a gap between the knife edge and the surface and to block X-rays outside the gap.

SUMMARY OF THE INVENTION

Embodiments of the present invention provide improved apparatus and methods for controlling the effective spot size and angular extent of a beam of radiation on a target area on the surface of a sample. The term "effective spot size," as used herein, refers to the size of the spot on the surface of the sample from which scattered radiation (reflected or otherwise) is received by a detector.

In some embodiments, a beam control assembly comprises a beam blocker, having a lower side that may be positioned in close proximity to the surface of the sample. The beam blocker contains front and rear slits, which are typically perpendicular to the lower side of the beam blocker. The beam blocker is positioned so that the slits are located on opposites sides of the target area and define a beam plane that contains the target area. In some of these embodiments, a beam limiter is positioned within the beam plain so as to block a portion of the plain. The beam limiter has a knife edge, which is transverse to the beam plane and typically protrudes below the lower side of the beam blocker. The beam control assembly may be used in various X-ray inspection techniques, such as XRR, XRD, and SAXS, as defined above.

In a typical XRR scenario, for example, the assembly is positioned so that the beam plane is aligned with an X-ray beam that is incident on the sample, and so that the knife edge is located adjacent to the target area and parallel to, but not touching, the surface of the sample. In this configuration, the transverse dimension of the X-ray spot formed on the surface and the transverse angular spread of the beam are limited by the width of the slits. The lateral dimension of the spot is limited by the knife edge. (Alternatively, the beam blocker may be used by itself to limit the transverse dimension of the spot, without the knife edge and/or with other means for limiting the lateral spot dimension.)

The spot size may thus be made very small, on the order of a few microns or less in the transverse direction. Furthermore, the beam blocker may be made wide enough, and the lower side of the beam blocker may be placed close enough to the sample surface so that all X-rays that are incident on the sample surface outside the area of the slits at angles above some minimum angle strike the beam blocker and are thus prevented from reaching the XRR detector. (X-rays below this minimum angle may be blocked separately by a dynamic shutter, as described in the Background of the Invention.) Use of the beam control assembly thus facilitates X-ray analysis of the sample surface with much finer spatial and angular resolution than could otherwise be achieved.

In other embodiments, transverse spread of the beam is controlled without necessarily using a beam blocker of the type described above. These latter embodiments are based on a discovery by the inventors that optical systems for focusing energetic radiation, such as X-rays, are commonly characterized by a transverse offset of the focal spot on the sample that varies as a function of elevation angle. This offset causes an effective increase in the spot size when the sample is irradiated over a range of angles, as in XRR systems that are known in the art.

To overcome this problem, in some embodiments of the present invention, the beam is controlled so as to impinge on the target area at each of a number of different elevation angles (or different angular sub-ranges in the vicinity of each these different elevation angle) in succession. The respective transverse offset of the beam is determined for each of the different angles, and a transverse correction is applied to either the beam or the sample, or both, to compensate for the respective offset. By maximizing the overlap between the irradiated spots on the sample at the different elevation angles in this manner, the effective transverse spread of the spot may be minimized.

There is therefore provided, in accordance with an embodiment of the present invention, a method for analysis of a sample, including:

directing a beam of radiation to impinge on a target area on a surface of the sample along a beam axis at each of a plurality of different elevation angles in succession;

determining, for each of the different angles, a respective offset of the beam in a direction transverse to the beam axis;

while directing the beam of radiation to impinge on the target area at each of the different elevation angles, applying a transverse correction to at least one of the beam and the sample to compensate for the respective offset; and sensing the radiation scattered from the sample while the beam irradiates the target area at each of the different elevation angles subject to the transverse correction.

In a disclosed embodiment, directing the beam includes directing the radiation to converge on the target area over a respective range of angles in a vicinity of each of the different elevation angles in he succession, and sensing the radiation includes resolving the scattered radiation as a function of elevation angle within the respective range. Typically, the radiation includes X-rays, and resolving the scattered radiation includes detecting a reflectometric spectrum of the X-rays, which is indicative of a characteristic of a thin film on the surface of the sample in the target area.

In some embodiments, directing the beam includes positioning a beam limiter between a source of the radiation and the sample, and adjusting the beam limiter to pass the radiation at each of the different elevation angles in succession while blocking the radiation that is emitted from the source at the other elevation angles. In one embodiment, positioning the beam limiter includes, for each given elevation angle, positioning a shutter so as to block the radiation that is emitted from the source at any of the elevation angles below the given elevation angle, and positioning a beam clipper so as to block the radiation that is emitted from the source at any of the elevation angles above the given elevation angle.

Typically, the beam impinges at the different elevation angles on respective spots within the target area, and applying the transverse correction includes choosing the transverse correction so as to maximize a mutual overlap of the respective spots. In a disclosed embodiment, the spots have a dimension in the direction transverse to the beam axis that is no greater than 50 µm.

Typically, applying the transverse correction includes shifting the at least one of the beam and the sample in the direction parallel to the surface of the sample.

There is also provided, in accordance with an embodiment of the present invention, apparatus for analysis of a sample, including:

a radiation source, which is configured to direct a beam of radiation toward a target area on a surface of the sample over a range of elevation angles;

a detector assembly, which is configured to sense the radiation that is scattered from the sample;

a beam limiter, which is configured to control the beam so that the radiation impinges on the target area along a beam axis at each of a plurality of different elevation angles in succession within the range;

a motion assembly, which is configured to shift at least one of the beam and the sample in a direction transverse to the beam axis; and a processor, which is coupled to record a respective offset of the beam in the direction transverse to the beam axis at each of the different elevation angles, and to control the motion assembly so as to apply a transverse correction to the at least one of the beam and the sample in order to compensate for the respective offset while the beam irradiates the target area at each of the different elevation angles.

There is additionally provided, in accordance with an embodiment of the present invention, a method for analysis of a sample, including:

directing a beam of radiation to impinge on a target area on a surface of the sample along a beam axis at a plurality of different elevation angles;

determining, for each of the different angles, a respective offset of the beam in a direction transverse to the beam axis;

sensing the radiation scattered from the sample at each of the different elevation angles in succession; and while sensing the radiation at each of the different elevation angles, applying a transverse correction to at least one of the beam and the sample in order to compensate for the respective offset at each of the different elevation angles.

The present invention will be more fully understood from the following detailed description of the embodiments thereof, taken together with the drawings in which:

DETAILED DESCRIPTION OF EMBODIMENTS

Figure 1:
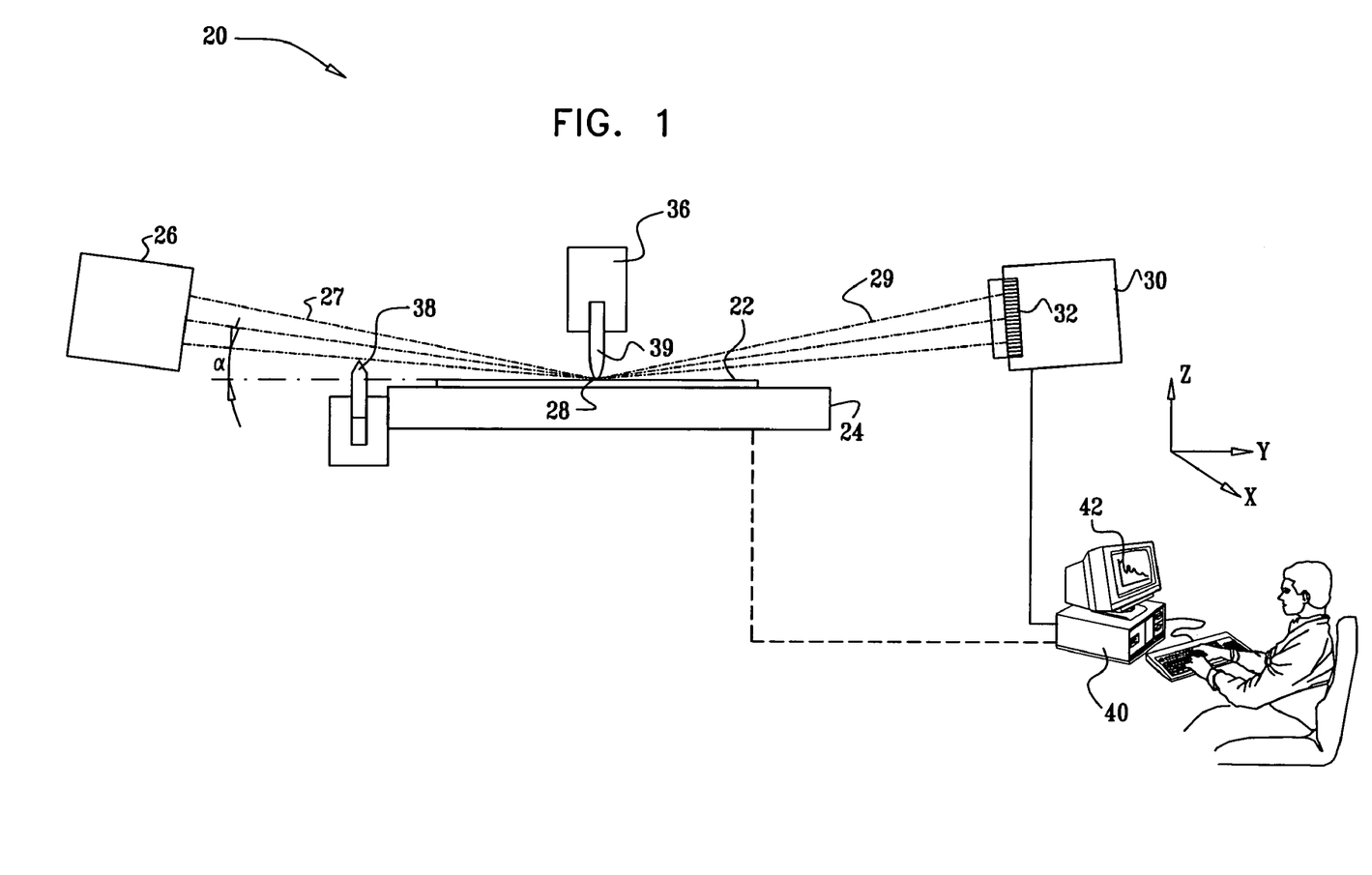
FIG. 1 is a schematic, side view of a system for XRR, in accordance with an embodiment of the present invention.

FIG. 1 is a schematic illustration of a system 20 for X-ray reflectometry (XRR) of a sample, such as a semiconductor wafer 22, in accordance with an embodiment of the present invention. System 20 can be used, for example, in a semiconductor fabrication facility, for identifying process faults and estimating process parameters at different stages of the wafer production process. Sample 22 is mounted on a mounting assembly, such as a motion stage 24, allowing accurate adjustment of the position and orientation of the sample. An X-ray source 26 irradiates a target area 28 on sample 22 with a converging beam 27 of X-rays. X-rays in a diverging beam 29 that is scattered from the sample are collected by a detector assembly 30, which typically comprises a detector array 32. Details of X-ray sources and detector assemblies that may be used in this configuration are described in the publications cited in the Background of the Invention.

For XRR measurement, converging beam 27 strikes area 28 at a grazing angle, typically over a range of incident angles from about 0° to 4.5°, although larger or smaller ranges may be used. In this configuration, detector assembly 30 collects diverging beam 29 over a range of angles in the vertical direction, as a function of elevation angle ($\phi$) between about 0° and at least 2°, and typically up to 3°. This range includes angles both below and above the critical angle of the sample for total external reflection, $\Phi_c$. (For clarity of illustration, the angular ranges shown in the figures are exaggerated, as is the elevation of source 26 and detector assembly 30 above the plane of sample 22. For convenience and clarity in this figure and in the description that follows, the sample plane is arbitrarily taken to be the X-Y plane, wherein the Y-axis is parallel to the projection of the axis of the X-ray beam on the sample surface. The Z-axis is in the vertical direction, perpendicular to the sample plane.)

A dynamic beam control assembly 36 and shutter assembly 38 are used to limit the angular extent of incident beam 27 of the X-rays in the vertical (Z) and horizontal (X) directions. The beam control assembly comprises a knife edge unit 39, which is described in detail with reference to the figures that follow. The heights of the knife edge unit and shutter relative to the sample surface are adjustable depending on the type of measurement being made and the range of measurement angles of interest.

A signal processor 40 receives and analyzes the output of detector assembly 30, so as to determine a distribution 42 of the flux of X-ray photons scattered from sample 22 as a function of angle at a given energy or over a range of energies. Typically, sample 22 has one or more thin surface layers, such as thin films, at area 28, and distribution 42 as a function of angle exhibits a structure that is characteristic of interference effects due to the outer layer and interfaces between the layers. Processor 40 analyzes characteristics of the angular distribution in order to determine characteristics of one or more of the surface layers of the sample, and may also serve as a system controller, to set and adjust the positions and configurations of the other system components.

In some XRR applications, such as testing of thin film layers on patterned semiconductor wafers, it is desirable to make the spot size of the X-ray beam in target area 28 very small, on the order of about 1-10 μm, at least in the transverse (X) dimension. With a focal spot this small, together with appropriate positioning of motion stage 24, the target area of the incident X-ray beam can be made to overlap a homogeneous area of the wafer, such as a scribe line between dies, aligned along the Y-axis. "Homogeneous" in this sense means that the surface layer and each of the underlying thin film layers of the wafer are uniform over the area of the focal spot. Under these conditions, the angular resolution of distribution 42 is enhanced, since the blurring effect of non-uniformities is reduced. The spatial resolution on the sample surface is, of course, increased, as well. These enhancements are achieved by means of the novel design of beam control assembly 36, as described hereinbelow.

Figure 2A:
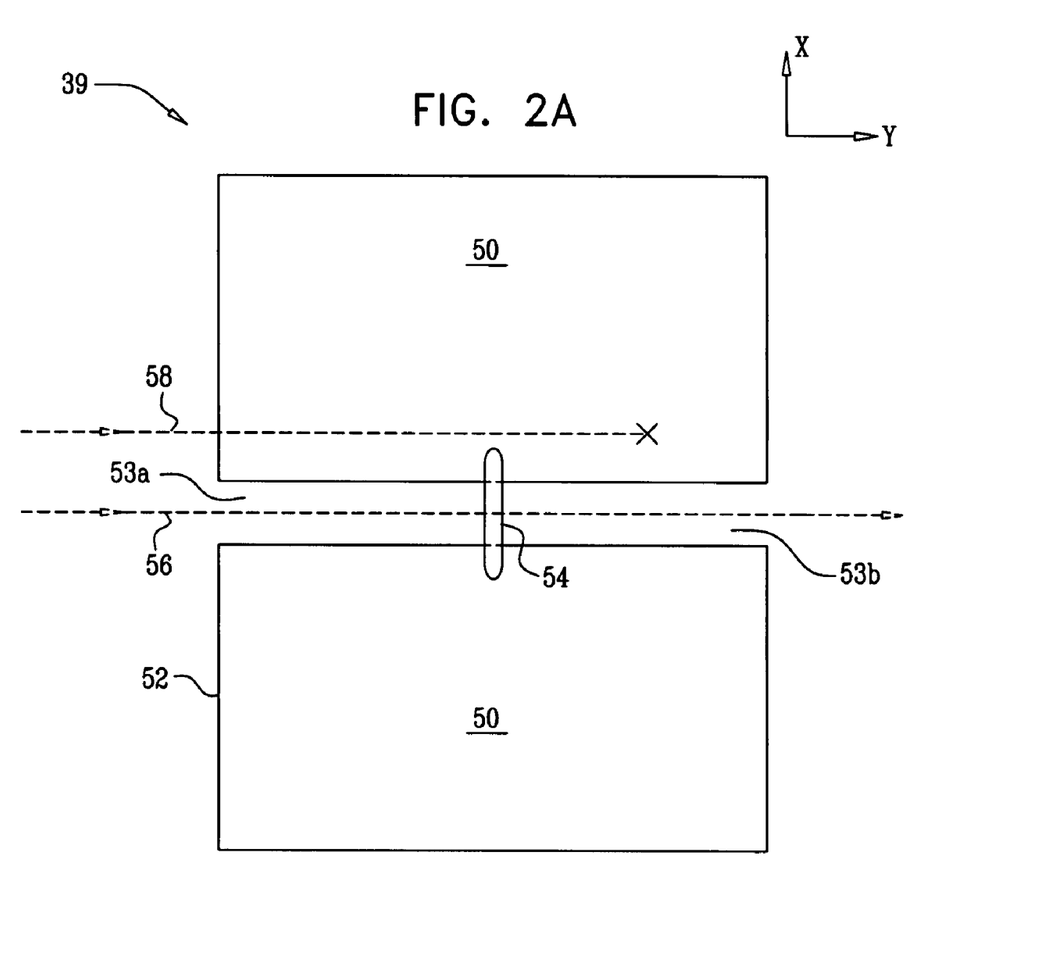
FIGS. 2A and 2B are schematic bottom and side views, respectively, of a beam control assembly, in accordance with an embodiment of the present invention.
Figure 2B:
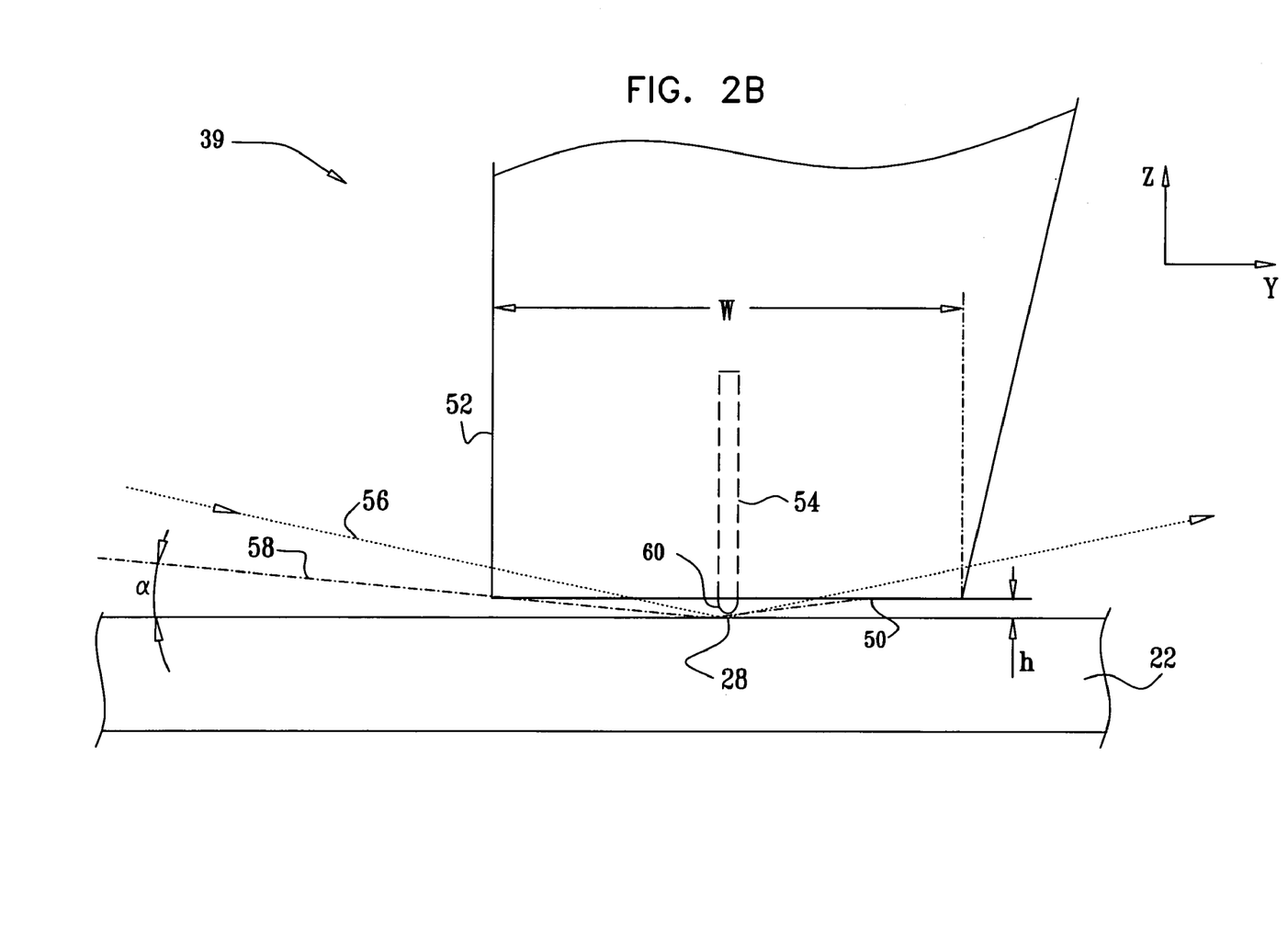

FIGS. 2A and 2B schematically show details of knife edge unit 39, in accordance with an embodiment of the present invention. FIG. 2A is a bottom view (as seen from the surface of wafer 22), while FIG. 2B is a side view. Unit 39 comprises a beam blocker 52, having a longitudinal slit 53 in which a beam limiter 54 is fitted. The beam limiter thus divides slit 53 into a front slit 53a and a rear slit 53b, which are referred to collectively simply as slit 53. The beam blocker and beam limiter are both made of metal or other X-ray absorbing materials. For example, the beam blocker and beam limiter may be made of tungsten-carbon with nickel additive.

Typically, the position (and particularly the height) of the beam limiter is adjustable relative to the beam blocker. Alternatively, although the beam blocker and beam limiter are shown and described, for the sake of clarity, as separate units, they may alternatively be integrally manufactured from a single piece of material. Further alternatively or additionally, although beam blocker 52 is shown in the figures as comprising solid, unitary blocks of material, other modes of construction may be used to achieve the structural and functional features that are described herein and recited in the claims. Exemplary alternative embodiments are described hereinbelow with reference to FIGS. 3A-3C and FIGS. 4A and 4B.

Beam blocker 52 has a lower side 50 that defines a plane, which is positioned in proximity to and a short distance above the surface of wafer 22. Although the lower side is shown in the figures as comprising a flat, unitary surface, parallel to the wafer surface, it may alternatively have recesses or other surface variations. In some embodiments, the lower side of the beam blocker may define a "virtual surface," i.e., a plane in space that is defined by the features of the beam blocker that are in proximity to the wafer surface. The alternative embodiments of FIGS. 3A-3C and FIGS. 4A and 4B have this sort of lower sides.

The distance between lower side 50 and the surface of wafer 22, marked h in FIG. 2B, may be on the order of about 10 μm, although larger or smaller distances may be used depending on application requirements. The width of beam blocker 52 in the axial (Y) direction, labeled W in FIG. 2B, is typically much greater than h. Slit 53 defines a beam plane, which is aligned with the incident X-ray beam in the Y-Z plane and thus passes through target area 28. The slit is typically on the order of 50 μm wide, but may be made as narrow as desired (and technically feasible) in order to limit the spread of the beam in the transverse (X) direction. For example, the transverse dimension of the slit may be 10 μm or less in order to limit the transverse dimension of the X-ray spot on sample 22 accordingly. Beam blocker 52 is positioned so that front slit 53a is located between source 26 and target area 28, while rear slit 53b is located between the target area and detector array 32. Thus, X-rays in the Y-Z plane within the slit, such as a ray 56, may pass through slit 53a over a range of elevation angles, reflect from the surface of wafer 22 beneath beam limiter 54, and exit from slit 53b to impinge on detector array 32.

X-rays outside slit 53 are either blocked by the front side of beam blocker 52, or penetrate the gap between the lower side of the beam blocker and the surface of the wafer. Those of the latter rays that strike the wafer surface at an elevation angle greater than a certain minimum angle $\alpha_{min}$, such as a ray 58, will reflect from the wafer and then impinge on the lower side of beam blocker 52, where they are absorbed. For a given W and h, it can be seen that $\alpha_{min} \cong 2h/W$. Rays incident at angles below $\alpha_{min}$ may be blocked by appropriate setting of shutter 38. In a typical XRR configuration, $\alpha_{min}$ may be set slightly below the critical angle $\Phi_c$ of wafer 22, i.e., $\alpha_{min}$=0.2°. Under these conditions, with h=10 μm, a beam blocker of width W≧5.73 mm will block substantially all rays above $\alpha_{min}$.

Alternatively, $\alpha_{min}$ may be varied depending on application requirements. For example, blocker 52 may be positioned higher above wafer 22, where it will not affect measurements made at low angles. Since XRR signals from the surface layer tend to be strong in any case at such low angles, any background effects that may be mixed into the signal from areas outside the desired measurement area (such as areas off the scribe line, when measurements are made along the scribe line) tend to be insignificant. Slit 53 will still limit the beam at higher angles, where background effects may be more problematic.

Beam limiter 54 is held by unit 39 in a plane transverse to slit 53, blocking at least the lower portion of the slit. The beam limiter has a knife edge 60 that typically protrudes below the lower side of beam blocker 52. Alternatively, in some applications, the beam limiter may be withdrawn so that the knife edge is above the lower side of the beam blocker. To minimize the lateral (Y) dimension of the X-ray spot on the surface of wafer 22, knife edge 60 may be positioned very close to the wafer surface, in the range of 1-3 μm from the surface, for example. In order to reduce the possibility of damage to the wafer and maintain an effective height of the knife edge over the wafer that is uniform over the entire angular range of interest (such as 0-4°), edge 60 may be rounded, as described in the above-mentioned U.S. Patent Application Publication 2006/0062351. For example, edge 60 may comprise a piece of tantalum wire of suitable diameter. Alternatively, edge 60 may be made by any other suitable process, may comprise any other suitable material (such as the tungsten/carbon/nickel material mentioned above), and may have any other suitable shape that is known in the art.

Figure 3A:
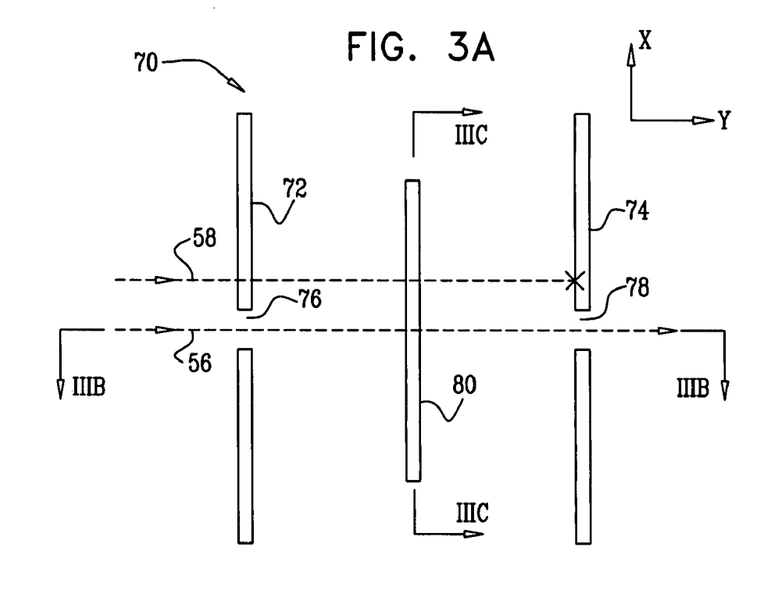
FIG. 3A is a schematic bottom view of a beam control assembly, in accordance with another embodiment of the present invention.
Figure 3B:
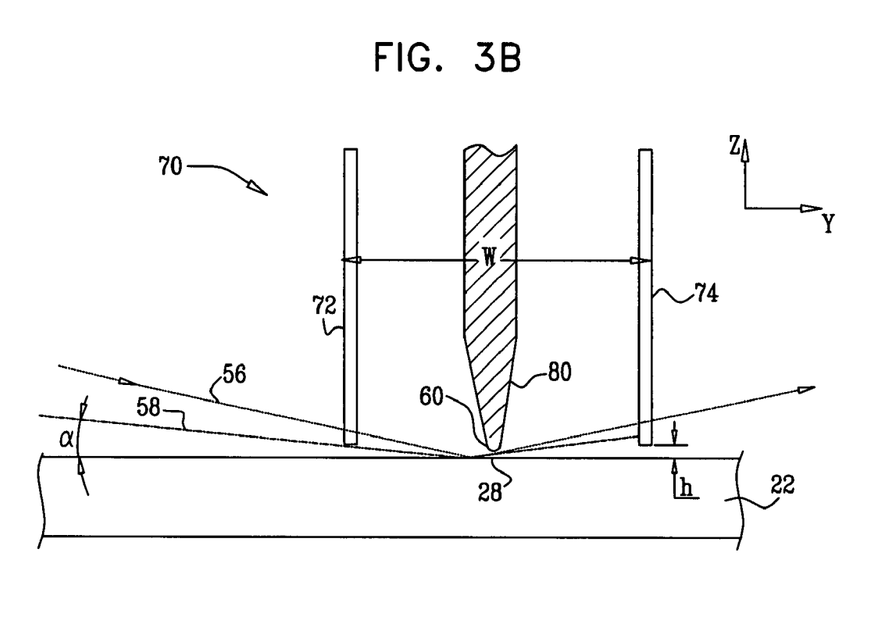
FIGS. 3B and 3C are schematic sectional views of the beam control assembly of FIG. 3A, taken along lines IIIB-IIIB and IIIC-IIIC in FIG. 3A, respectively.
Figure 3C:
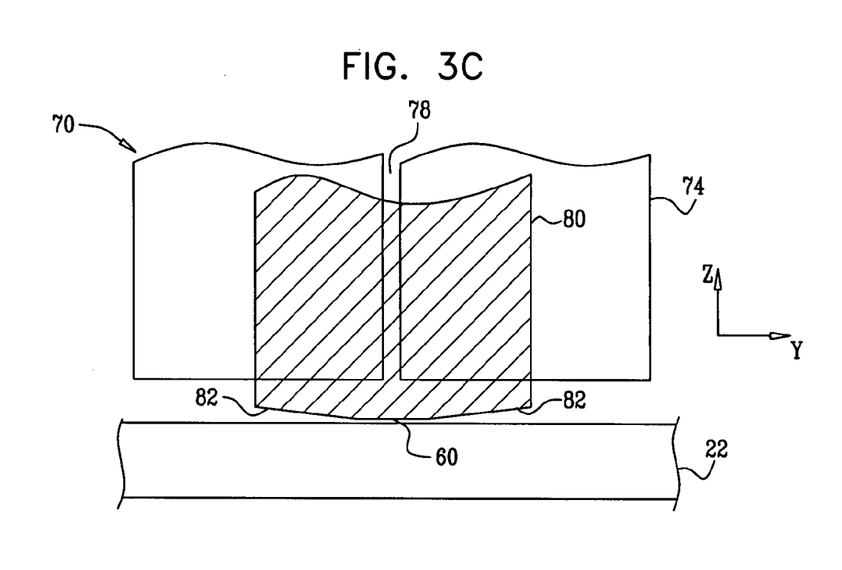

Reference is now made to FIGS. 3A-3C, which schematically illustrate a beam control assembly 70, in accordance with another embodiment of the present invention. Assembly 70 may be used in place of beam control assembly 39 in the system of FIG. 1. FIG. 3A is a bottom view (looking upward along the Z-axis from wafer 22) of assembly 70, while FIGS. 3B and 3C are sectional views, taken along lines IIIB-IIIB and IIIC-IIIC, respectively in FIG. 3A.

The principles of operation of assembly 70 are similar to those of assembly 39, and like elements are marked with the same numbers in the various figures. In assembly 70, however, front and rear blocker units 72 and 74 take the place of beam blocker 52. The blocker units have respective front and rear slits 76 and 78, which fulfill the role of slits 53a and 53b. Typically, blocker units 72 and 74 are aligned and held together in a mount, which moves the units up and down in relation to wafer 22. The lower edges of the two blocker units make the lower side of the beam blocker in this case, and define a surface that is positioned at the height h above the wafer. Alternatively, the two blocker units may be individually adjustable.

A beam limiter 80 is positioned between blocker units 72 and 74 transverse to the plane of slits 76 and 78 and blocking at least part of the radiation in this plane. Typically, edge 60 of the beam limiter is positioned in close proximity to the surface of wafer 22, below the lower surface defined by the lower edges of the blocker units. Alternatively, beam limiter 80 may be withdrawn to a higher position.

As shown in FIG. 3C, beam limiter 80 may be considerably wider than slits 76 and 78. This sort of wide beam limiter is helpful in reducing the amount of stray radiation that may scatter beneath the beam blocker units and strike detector array 32. On the other hand, the wide beam limiter may create difficulties in positioning edge 60 parallel and very close to the wafer surface, particularly since the wafer surface may not be perfectly flat. To ameliorate such difficulties, edge 60 may be formed only in the central part of beam limiter 80, while outer edges 82 angle slightly upward, as shown in the figure. Although for the sake of visual clarity, outer edges 82 are angled sharply relative to edge 60 in FIG. 3C, in practice the outer edges may angle up by much smaller angles, on the order of 0.1° to 1°.

Figure 4A:
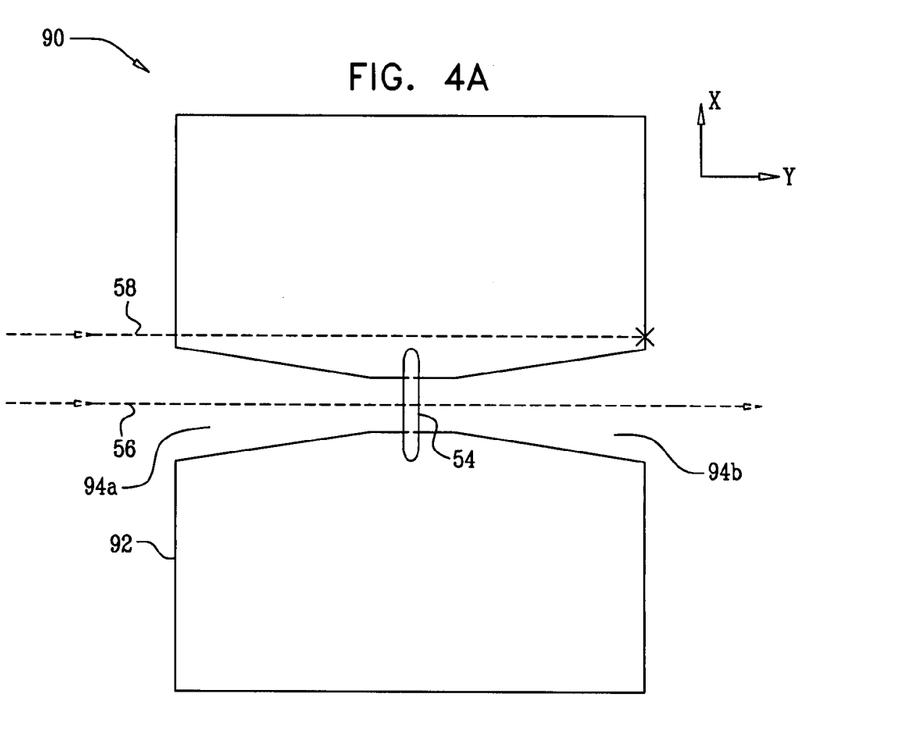
FIGS. 4A and 4B are schematic bottom and side views, respectively, of a beam control assembly, in accordance with yet another embodiment of the present invention.
Figure 4B:
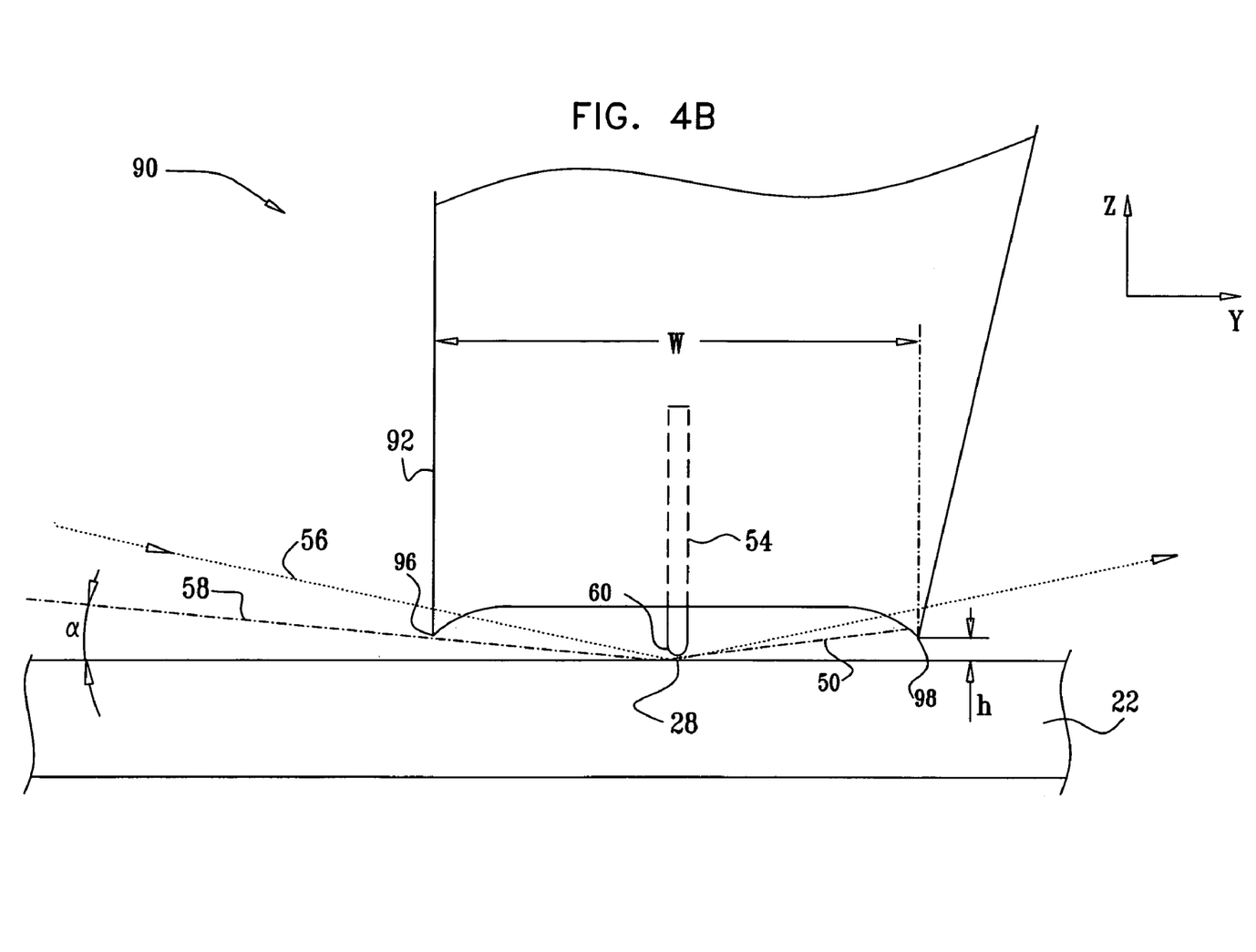

FIGS. 4A and 4B schematically illustrate a beam control assembly 90, in accordance with yet another embodiment of the present invention. Assembly 90 may be used in place of assembly 39 in the system of FIG. 1, and like features are again identified by the same numbers. FIG. 4A is a bottom view of assembly 90, while FIG. 4B is a side view.

Assembly 90 comprises a beam blocker 92 having a slit 94 passing therethrough. As in beam blocker 39, slit 94 is divided into front and rear slits 94a and 94b by beam limiter 54. Slits 94a and 94b have profiles of non-uniform width in the X-direction, as shown in FIG. 4A, with relatively wide outer ends at the front and rear surfaces of the beam blocker, and a narrow waist in the center. In this example, the slit profiles are triangular, although other non-uniform profiles may similarly be used. Since converging beam 27 may converge in the X-direction (together with the Z-direction convergence shown in FIG. 1), the triangular slits can be useful in increasing the amount of beam power that is incident on target area 28 and is reflected onto detector array 32.

As shown in FIG. 4B, the lower side of beam blocker 92 is not flat, but is rather recessed for convenience of alignment with the surface of wafer 22. The lower surface, at height h above the wafer surface, is in this case defined by front and rear lower edges 96 and 98. The shape of beam blocker 92 (as well as the shapes of the other beam blockers and beam limiters shown above) is presented solely by way of example, and alternative shapes that may be used to similar effect will be apparent to those skilled in the art and are considered to be within the scope of the present invention.

Figure 5:
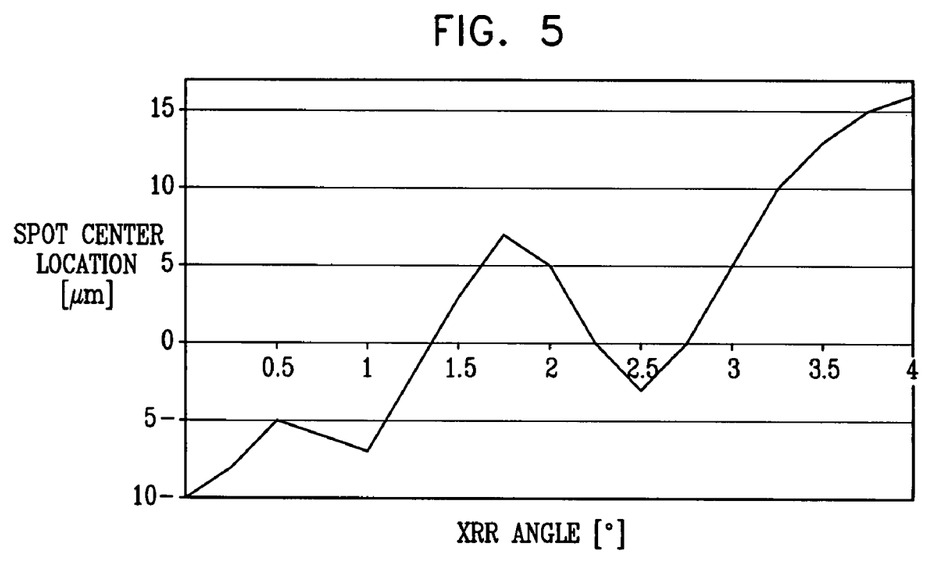
FIG. 5 is a schematic plot of transverse beam offset as a function of elevation angle.

FIG. 5 is a schematic plot of beam offset as a function of elevation angle, in accordance with an embodiment of the present invention. In order to create this plot, the beam from source 26 (FIG. 1) irradiated a test surface, and detector assembly 30 measured the intensity of the reflected beam as a function of elevation angle. The strength of the signal output by each element of detector assembly 32 was monitored as a vertical knife edge (not shown in the figures) was moved gradually in the X-direction across the incident beam. The X-coordinate of the knife edge at which the signal from a given detector element dropped to half its original strength was taken to be the center of the incident beam for the corresponding elevation angle. Thus, processor 40 is able to determine the transverse (X-direction) offset of the center of the spot formed in target area 28 by beam 27 for different elevation angles.

If X-ray source 26 were optically perfect, the beam center would have the same X-coordinate regardless of elevation angle. It can be seen in FIG. 5, however, that the beam center shifts by a total of about 25 μm as the elevation increases from 0° to 4°. This shift is evidently due to aberrations in the X-ray optics that are used to focus beam 27 onto target area 28. (The method for correcting the shift that is described hereinbelow, however, may be used regardless of the cause of the shift.) The shift, if uncontrolled, effectively spreads the spot on target area 28 by the total amount of the shift. In other words, if the transverse size of the focal spot at a single elevation angle is 40-50 μm, the effective spot size over the range of angles between 0° and 4° will be approximately 65-75 μm. The detection resolution of system 20 is degraded accordingly.

Figure 6A:
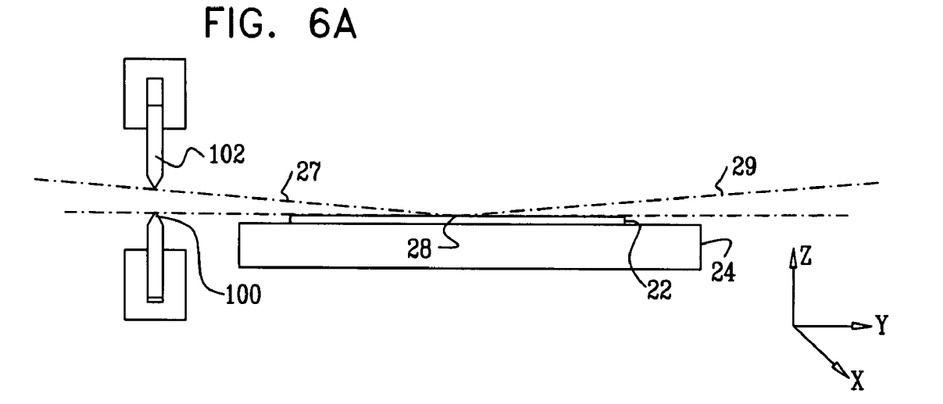
FIGS. 6A-6C are schematic side views of a beam limiter in three different angular settings, in accordance with an embodiment of the present invention.
Figure 6B:
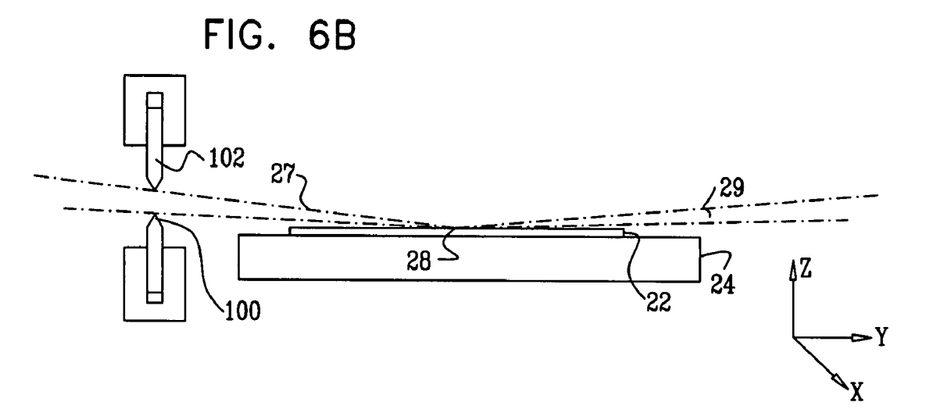
Figure 6C:
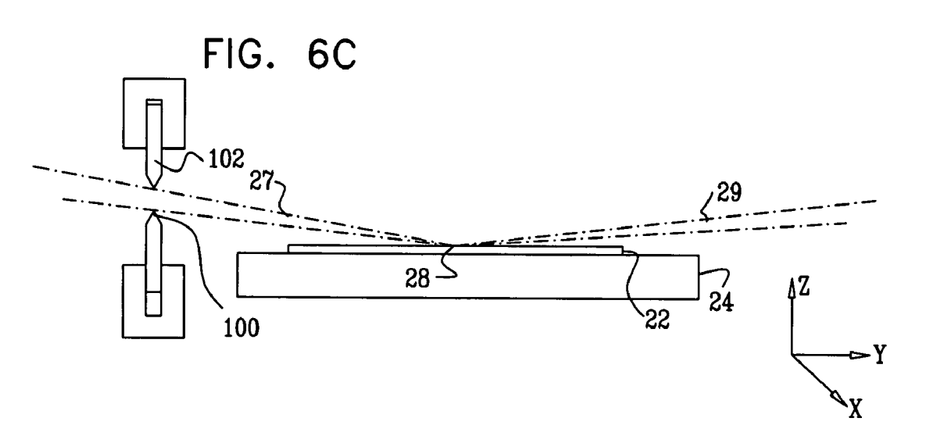

FIGS. 6A-6C are schematic side views of elements of a beam limiter and motion control assembly that may be used to resolve this problem, in accordance with an embodiment of the present invention. The beam limiter in this embodiment comprises a shutter 100 and a beam clipper 102, which may be similar in construction and operation to the shutter described above. Alternatively, other types of beam limiting devices may be used to achieve the purposes of this beam limiter, as will be apparent to those skilled in the art.

In each of FIGS. 6A-6C, shutter 100 and clipper 102 are adjusted to admit radiation over a different range of elevation angles within beam 27, while blocking the radiation at angles outside the range. Thus, for example, FIG. 6A shows an adjustment configuration in which radiation in the range between 0° and 1° is permitted to impinge on target area 28, while the adjustment configurations of FIG. 6B and FIG. 6C permit radiation to impinge in the 1-2° range and the 2-3° range, respectively. (The angles are exaggerated in these figures for the sake of visual clarity.) Alternatively, the beam limiter may be controlled to admit radiation over a smaller or larger number of different ranges, which may be larger or smaller than those listed above.

Processor 40 (FIG. 1) steps the beam limiter through the different elevation ranges in succession. For each range, the processor determines the value of the transverse beam offset that is associated with the elevation angle of the corresponding beam axis. These offset values are typically tabulated in advance, using a calibration procedure such as that described above with reference to FIG. 5. The processor may use the offset value measured at the center of each range, for example, or it may alternatively use an average value of the offset over each range. It then drives a motion assembly, such as translation stage 24, to apply a transverse correction to the position of wafer 22 that precisely compensates for the offset. In other words, referring to the calibration data shown in FIG. 5, for example, for XRR measurement in the 0-1° range of FIG. 6A, the processor will drive stage 24 to shift −5 μm in the X-direction relative to a zero-reference position. It will then drive the stage to +3 μm relative to the zero-reference position for measurement in the 1-2° range of FIG. 6B, and so forth. Alternatively, the motion assembly may shift the X-ray source to compensate for the offset, instead of or in addition to shifting wafer 22.

As a result of this calibration and correction procedure, the mutual overlap of the spots formed in target area 28 by beam 27 at the different elevation angles will be maximized. Therefore, the effective transverse spot size will be limited to a value that is close to the focusing limit of the X-ray optics without the elevation-dependent aberration.

Alternatively, other means may be used to limit the range of elevation angles over which the reflected radiation is sensed. For example, in one embodiment (not shown in the figures), the beam limiter is positioned so as to limit beam 29 to the desired range of angles, rather than beam 27 as shown in the figure. As a further alternative, the range of elevation angles may be limited by selection of different elements or groups of elements of detector array 32 in succession, while adjusting the transverse correction appropriately.

Although features of system 20 are described hereinabove with specific reference to XRR, the principles of the present invention, and particularly of the beam control assemblies shown above, may similarly be applied in other areas of X-ray analysis, such as SAXS and XRD. Furthermore, these principles are not limited to the X-ray field, but rather may be applied in analysis using electromagnetic radiation in other ranges of wavelength, such as gamma radiation, as well as particle beam irradiation, that impinges on a sample at an angle. It will thus be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

The invention claimed is:

1. A method for analysis of a sample, comprising:
   directing a beam of radiation to impinge on a target area on a surface of the sample along a beam axis at each of a plurality of different elevation angles in succession;
   determining, for each of the different angles, a respective offset of the beam in a direction transverse to the beam axis;
   while directing the beam of radiation to impinge on the target area at each of the different elevation angles, applying a transverse correction to at least one of the beam and the sample to compensate for the respective offset; and
   sensing the radiation scattered from the sample while the beam irradiates the target area at each of the different elevation angles subject to the transverse correction.

2. The method according to claim 1, wherein directing the beam comprises directing the radiation to converge on the target area over a respective range of angles in a vicinity of each of the different elevation angles in succession, and wherein sensing the radiation comprises resolving the scattered radiation as a function of elevation angle within the respective range.

3. The method according to claim 2, wherein the radiation comprises X-rays, and wherein resolving the scattered radiation comprises detecting a reflectometric spectrum of the X-rays, which is indicative of a characteristic of a thin film on the surface of the sample in the target area.

4. The method according to claim 1, wherein directing the beam comprises positioning a beam limiter between a source of the radiation and the sample, and adjusting the beam limiter to pass the radiation at each of the different elevation angles in succession while blocking the radiation that is emitted from the source at the other elevation angles.

5. The method according to claim 4, wherein positioning the beam limiter comprises, for each given elevation angle:
   positioning a shutter so as to block the radiation that is emitted from the source at any of the elevation angles below the given elevation angle; and
   positioning a beam clipper so as to block the radiation that is emitted from the source at any of the elevation angles above the given elevation angle.

6. The method according to claim 1, wherein the beam impinges at the different elevation angles on respective spots within the target area, and wherein applying the transverse correction comprises choosing the transverse correction so as to maximize a mutual overlap of the respective spots.

7. The method according to claim 6, wherein the spots have a dimension in the direction transverse to the beam axis that is no greater than 50 μm.

8. The method according to claim 1, wherein applying the transverse correction comprises shifting the at least one of the beam and the sample in the direction parallel to the surface of the sample.

9. Apparatus for analysis of a sample, comprising:
a radiation source, which is configured to direct a beam of radiation toward a target area on a surface of the sample over a range of elevation angles;
a detector assembly, which is configured to sense the radiation that is scattered from the sample;
a beam limiter, which is configured to control the beam so that the radiation impinges on the target area along a beam axis at each of a plurality of different elevation angles in succession within the range;
a motion assembly, which is configured to shift at least one of the beam and the sample in a direction transverse to the beam axis; and
a processor, which is coupled to record a respective offset of the beam in the direction transverse to the beam axis at each of the different elevation angles, and to control the motion assembly so as to apply a transverse correction to the at least one of the beam and the sample in order to compensate for the respective offset while the beam irradiates the target area at each of the different elevation angles.

10. The apparatus according to claim 9, wherein the radiation source is configured to direct the radiation to converge on the target area over a respective range of angles in a vicinity of each of the different elevation angles in succession, and wherein the detector assembly is configured to resolve the scattered radiation as a function of elevation angle within the respective range.

11. The apparatus according to claim 10, wherein the radiation comprises X-rays, and wherein the detector assembly is configured to detect a reflectometric spectrum of the X-rays, which is indicative of a characteristic of a thin film on the surface of the sample in the target area.

12. The apparatus according to claim 9, wherein the beam limiter is adjustable to pass the radiation at each of the different elevation angles in succession while blocking the radiation that is emitted from the radiation source at the other elevation angles.

13. The apparatus according to claim 12, wherein the beam limiter comprises:
a shutter, which is positionable so as to block the radiation that is emitted from the source at any of the elevation angles below the given elevation angle; and
a beam clipper, which is positionable so as to block the radiation that is emitted from the source at any of the elevation angles above the given elevation angle.

14. The apparatus according to claim 9, wherein the beam impinges at the different elevation angles on respective spots within the target area, and wherein the processor is configured to apply the transverse correction so as to maximize a mutual overlap of the respective spots.

15. The apparatus according to claim 14, wherein the spots have a dimension in the direction transverse to the beam axis that is no greater than 50 μm.

16. The apparatus according to claim 9, wherein the motion assembly is configured to shift the at least one of the beam and the sample in the direction parallel to the surface of the sample.

17. A method for analysis of a sample, comprising:
directing a beam of radiation to impinge on a target area on a surface of the sample along a beam axis at a plurality of different elevation angles;
determining, for each of the different angles, a respective offset of the beam in a direction transverse to the beam axis;
sensing the radiation scattered from the sample at each of the different elevation angles in succession; and
while sensing the radiation at each of the different elevation angles, applying a transverse correction to at least one of the beam and the sample in order to compensate for the respective offset at each of the different elevation angles.

* * * * *